(12) United States Patent
Roth et al.

(10) Patent No.: US 6,201,607 B1
(45) Date of Patent: Mar. 13, 2001

(54) BLOOD FLUID CHARACTERISTICS ANALYSIS INSTRUMENT

(75) Inventors: G. Thomas Roth, Fairfield; Gregory P. Paolini, Norwalk, both of CT (US)

(73) Assignee: MIT Development Corporation, Trumbull, CT (US)

( * ) Notice: Subject to any disclaimer, the term of this patent is extended or adjusted under 35 U.S.C. 154(b) by 0 days.

(21) Appl. No.: 09/379,130

(22) Filed: Aug. 20, 1999

Related U.S. Application Data (62) Division of application No. 09/059,082, filed on Apr. 13, 1998.

(51) Int. Cl.[7] .......................... G01N 21/55; G01N 33/48
(52) U.S. Cl. .............................................. 356/445; 356/39
(58) Field of Search .................................. 356/445–448, 356/39–43

(56) References Cited

U.S. PATENT DOCUMENTS

| | | | |
|---|---|---|---|
| 4,523,853 | 6/1985 | Rosenbladt et al. | 356/446 |
| 4,552,458 | 11/1985 | Lowne | 356/446 |
| 4,627,445 | 12/1986 | Garcia et al. | 128/770 |
| 4,632,559 | 12/1986 | Brunsting | 356/416 |
| 4,637,403 | 1/1987 | Garcia et al. | 128/770 |
| 4,787,398 | 11/1988 | Garcia et al. | 128/770 |
| 4,985,205 | 1/1991 | Fritsche et al. | 422/56 |
| 5,039,225 | 8/1991 | Uekusa | 356/448 |
| 5,114,350 | 5/1992 | Hewett | 435/288 |
| 5,279,294 | 1/1994 | Anderson et al. | 128/633 |
| 5,321,492 | 6/1994 | Detwiler et al. | 356/73 |
| 5,424,035 | 6/1995 | Hones et al. | 422/55 |
| 5,424,545 | 6/1995 | Block et al. | 250/343 |
| 5,518,689 | 5/1996 | Dosmann et al. | 422/82.05 |
| 5,563,042 | 10/1996 | Phillips et al. | 435/14 |
| 5,597,532 | 1/1997 | Connolly | 422/58 |
| 5,611,999 | 3/1997 | Dosmann et al. | 422/82.05 |

*Primary Examiner*—Frank G. Font
*Assistant Examiner*—Amanda Merlino
(74) *Attorney, Agent, or Firm*—St. Onge Steward Johnston & Reens LLC (57) ABSTRACT

An apparatus for enhancing the analysis of light reflected from a blood exposed reagent is described. Light from sources, such as LED's, is used to detect the levels of glucose and fructosamine in the blood exposed reagent. A special optical arrangement is used to obtain optical signals indicative of the optically sensitive chemicals in the reagent. The optical beams from respective LED's are directed at a common surface of an optical element used to redirect the light onto the reagent and reflect portions onto a reference detector. A main detector is strategically located adjacent a surface of the optical element to detect reflections from the reagent. A control circuit is described with which the light from the LED light sources can be held at substantially constant levels despite factors tending to cause light level changes.

5 Claims, 6 Drawing Sheets

BLOOD FLUID CHARACTERISTICS ANALYSIS INSTRUMENT

This application is a Division of application Ser. No. 09/059,082, filed Apr. 13, 1998.

FIELD OF THE INVENTION

This invention generally relates to body fluid analysis instruments and more particularly to a blood analysis device for determining levels of different types of sugar in a blood sample.

BACKGROUND OF THE INVENTION

Devices for enabling patients to test their own blood are well known in the art. One such device is shown in U.S. Pat. No. 4,552,458, to Lowne, which deals with a compact reflectometer to enable the exposure of a reagent to different light beams, one red and one green. The light beams are folded by a reflecting surface, which redirects the beams through a transparent glass plate onto a reagent strip. Light is reflected back from the strip along a similar folded path onto a detector located in the same plane as the light sources.

Other patents describing various optical arrangements for illuminating and detecting the light reflected from reagent strips are U.S. Pat. No. 4,632,559, to Miles, for an optical read head for measuring non-specular, i.e. non-mirror-like, reflections from a reagent test strip; U.S. Pat. No. 4,787,398, to Garcia, for a glucose medical monitoring system and U.S. Pat. No. 4,985,205 for a test carrier analysis system.

The latter '205 patent describes a reference measurement using the same optical elements by using the same reference layer so as to avoid a two tier testing process. The reference measurement uses two LED's for illuminating the same color formation layer from different directions. The LED's are preferably activated successively so that the measurements can then be averaged.

U.S. Pat. No. 5,039,225 describes a device for measuring optical density with a light transmissive plate inserted between the light source and the surface being measured. The light is directed at an angle relative to a surface of the plate so that a portion is reflected back to a detector for obtaining a reference measurement while another detector is oriented to detect diffuse light for analysis.

Other patents related to body fluid analysis are U.S. Pat. Nos. 5,114,350; 5,279,294 for a glucose diagnostic device which can fit inside a shirt pocket; U.S. Pat. No. 5,321,492 using a dual function read head for a glucose level detector; U.S. Pat. No. 5,424,035 for a glucose test strip positioning structure; U.S. Pat. No. 5,424,545 for a non-invasive spectro-photometric technique to determine glucose levels; U.S. Pat. Nos. 5,518,689 and 5,611,999 for a diffused light reflectance technique wherein the reagent sample is held at a particular angle relative to the incident beam to obtain an improved performance; U.S. Pat. Nos. 5,563,042 and 5,597,532 for particular types of glucose test strips.

None of the these patents describe or disclose a small personally useable body fluid diagnostic instrument with which both glucose and fructosamine levels in a blood sample can be detected.

SUMMARY OF THE INVENTION

Accordingly, one object of the present invention is to provide a diagnostic apparatus for determining the levels of both glucose and fructosamine in a blood sample using respectively different reagents in strips and which undergo a color change when exposed to a blood sample containing glucose or fructosamine. A light source is used to illuminate the blood exposed reagent strip to enable a light detector to determine what color is reflected by the strip.

It is a further object of the invention to enable a precise compensation for wavelength changes in a light source, which is used to detect the level of a chemical in a reacted reagent by sensing color changes in the reflectance characteristics of a reacted reagent.

When the wavelength of the light source increases, which can be the result of an increase in the temperature of the LED used for the light source or to a change in the drive current to the LED, the reflectance measured with a light detector, whose sensitivity increases with wavelength (i.e. provides more output signal) is also increased. With no control over the light source's optical output power, the reflectance measured with this type of detector would tend to increase as the wavelength increase, causing an erroneous measurement.

One apparatus for practicing the invention includes a control loop with which an accurate compensation for variations in the characteristics of a light source used in the analysis of the reagent can be obtained for a reliable measurement of the blood sample. This is achieved with one embodiment in accordance with the invention by employing a reference detector to control the amplitude output level from the light source.

When the reference detector has a particular response characteristic to different wavelengths generated by the light source used to analyze the blood exposed reagent strip, this response can be used to compensate for the wavelength changes in the light source. Hence, as the wavelength of the light source alters over time, a reference detector compensates for this change to produce a correspondingly changed output level from the light source. When a main detector, sensitive to the reflectance from the blood exposed reagent strip, is a similar detector as the reference detector, the output signal from the main detector will exhibit the same changed level and thus produce a constant output signal despite the change in wavelength of the light source.

Different types of light detectors can be used for the reference and main detectors so as to achieve different compensations useful for the compensation for other portions of the optical system used in the apparatus. For example, compensation for the sensitivity of the transmittance of the optical system to different wavelengths can be obtained in this manner, as well different dyes can be used in the optical system to force a different wavelength response to achieve a particular response characteristic for the reagent reflected light detection system.

One particular apparatus for practicing the invention comprises a housing, an optical beam generating structure comprising an optical element, two spaced apart light beam generators selected to enable the investigation of different reagents on strips, a reference detector positioned to detect and control light from a light source, and a main detector to detect light reflections from a reagent strip aligned with an aperture and passing through the optical element. The output signal from the reference detector is used in a control loop to regulate the light output from the light source.

It is, therefore, a further object of the invention to provide a diagnostic apparatus of the above character wherein an automatic compensation for changes in the wavelength from the light source is obtained for an accurate detection of the color change in a reagent strip.

It is yet another object of the invention to provide a diagnostic apparatus of the above character wherein the optical beam generating structure includes a base plate and a cover plate adapted to intermesh with each other to form an optical path enclosure, the optical path enclosure including two converging paths retaining two different light wavelength beam generators, the two converging paths encompassing the two beam axes.

The above objects and advantages of the invention are accomplished by a diagnostic apparatus for determining the levels of both glucose and fructosamine in a blood sample using respectively different reagent strips with reagents that undergo a color change when exposed to a blood sample containing glucose or fructosamine. One apparatus in accordance with the invention comprises a housing, an optical beam generating structure, a reference detector and a main detector. The optical beam generating structure further comprises an optical element and two spaced apart light beam generators for illuminating respectively different reagent strips. The housing has a surface for receiving the reagent strips and an optical aperture through which an optical beam from inside the housing can illuminate the reagent on a test strip aligned with the aperture.

The optical beam generating structure is positioned inside the housing and produces the optical beam through the optical aperture with light from a reagent strip being reflected back through the aperture for detection. The optical beam generating structure has an optical element, such as a prism, which has a front surface, an upper surface, a bottom surface and an inclined reflecting surface, which can be either an internal or external surface, and which extends at a reflecting angle relative to the front surface. The optical element's upper surface is juxtaposed with respect to the aperture. The optical beam generating structure also has two spaced apart light beam generators each producing an optical beam along an axis. Each of the beam axes are oriented at angles relative to normals to the front surface of the optical element. The two light beam generators produce optical beams which reflect from the front surface of the optical element along reference axes and further refract towards the inclined reflecting surface for reflection thereby to the aperture.

The reference detector is positioned to detect reflections along the reference axes and to produce a reference signal in response to the reflections. The main detector is juxtaposed with respect to the bottom surface of the optical element to detect light reflections passing through the optical element from a reagent strip that is aligned with the aperture. The reference signal is used to regulate the light output levels from the light beam generators and provide compensation for wavelength changes.

The optical structure can further include a base plate and a cover plate adapted to intermesh with each other to form an optical enclosure. The optical enclosure includes two converging paths respectively retaining the two light beam generators with the two converging paths respectively encompassing the two beam axes.

DETAILED DESCRIPTION OF DRAWINGS

With reference to FIGS. 1–7, the housing of the diagnostic apparatus 10 comprises an upper housing 12 connected to a lower housing 14, which retains a printed circuit board 15 on which an optical assembly 17 is mounted. The optical assembly 17 includes optical devices and an optically sealed housing 19 formed of a base plate 21 and an intermeshing upper enclosure 23 having an aperture 26' located in alignment with aperture 26 in surface 24 of a reagent strip receiving assembly 29 of apparatus 10. The assembly 29 slides onto upper enclosure 23 starting at its front edge 31.

A user begins by placing the blood exposed reagent over aperture 26 and then a blood sample 22 upon a reagent pad 20 to make a diagnosis. The reagent pad 20 is subjected to a light beam 25 alternately from light beam generators 28.1 and 28.2 located inside the optical enclosure 19 and light reflections 27 from the blood exposed reagent material are incident onto a main photo detector 32. The light produced by the light sources 28.1 and 28.2 have wavelengths selected to enhance the ability to detect respectively the presence of glucose and fructosamine in the blood exposed reagent 22.

The spaced apart light sources 28.1 and 28.2 each produce a light beam along beam axes 44.1 and 44.2 respectively. These beams are incident onto the front surface 38 of an optical element 30. The optical element 30 is used to direct the optical beam 25 from each of the light generators 28 onto blood reacted segment 22 of the reagent strip 18. The optical element can be a prism having a front surface 38, an upper surface 42, a bottom surface 41 and an inclined internal reflecting surface 40. Other optical elements can be used to direct light onto the reagent strip 18. The optical element 30 extends up into an aperture 26' of the cover plate 14 so as to be essentially flush with the upper surface 43 of upper enclosure 23. This is achieved by forming the prism element 30 by molding it onto the upper enclosure 23.

Each of the beam axes 44 is oriented at an angle relative to a normal to the front surface 38 of the optical element 30. The reflected portion of an optical beam 25 travels along a reference axis 46 to be incident on a reference detector 34. The part of the optical beam 25 that refracts into the optical element 30 is directed onto an inclined inner reflecting surface 40 of the optical element 30. The inner reflecting surface 40 has a reflection angle relative to the front surface 38 so that the optical beam 25 is reflected up through the upper surface 42 of optical element 30 and through apertures 26' and 26 onto the blood exposed reagent segment 22.

The optical apertures 26 26' comprise openings in both the upper enclosure housing 23 and reagent strip receiver 29 and thus limit incidence of light onto segment 22 to the optical beam 25. When a reagent strip 18 with reagent pad 20 and a blood sample 22 is placed upon the surface 24, the optical beam 25 travels through apertures 26, 26', reflect off the blood reacted reagent pad .20 and travel back through the apertures 26 and 26'.

The main detector 32, which is juxtaposed with respect to the bottom surface 41 of the optical element 30, detects the reflections 27 caused by optical beam 25 from the segment 22 and produces an output signal for subsequent analysis to determine the presence and quantity of predetermined chemicals in the blood, such as glucose and fructosamine.

The part of the optical beams 25 that are reflected off the front surface 38 of the optical element 30 travel along the reference axes 46 to reference detector 34. The reference detector 34 generates a signal indicative of the magnitude of the optical beam 25's intensity and this used, as explained with respect to FIGS. 15 and 16 to maintain the intensity output from the corresponding light source at a constant level. A mask 36 is placed between the optical element 30 and the reference detector 34 to isolate the reference detector 34 from extraneous light signals produced by the incidence of and reflections from an optical beam 25 on various surfaces inside the apparatus 10.

The paths through which the light beams 25 travel through the light sealed enclosure formed by upper enclosure 23 and lower base plate 21 are determined by various intermeshing walls 47 and edges 49. Some of these walls and edges are formed into the base plate 21 and others are formed into the upper enclosure 23 as is evident from the views in FIGS. 2, 5, 6 and 7. When the base plate 21 and the cover plate 23 are intermeshed to form an optical enclosure 33 (see FIGS. 2, 6 and 7), the optical enclosure includes two converging channels 50.1 and 50.2 for reflected beams 46.1 and 46.2. These converging channels 50 terminate at the reference detector 34 so that it can detect the reflections from the respective light beam generators 28.1 and 28.2.

The optical beams 25 are preferably created by two light emitting diodes (LED). One optical beam 25 from light source 28.1, for example, is a red LED and is used to detect the presence of glucose. The other optical beam 25 from light source 28.2 is a green LED and is used to detect the presence of fructosamine.

Figure 1:
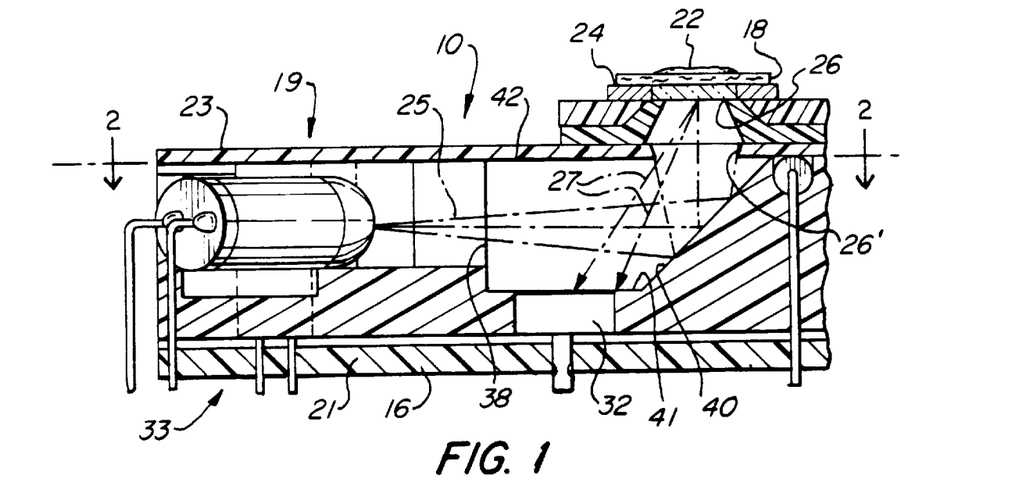
FIG. 1 is a partial section view in elevation of a portion of the instrument of FIG. 3.
Figure 2:
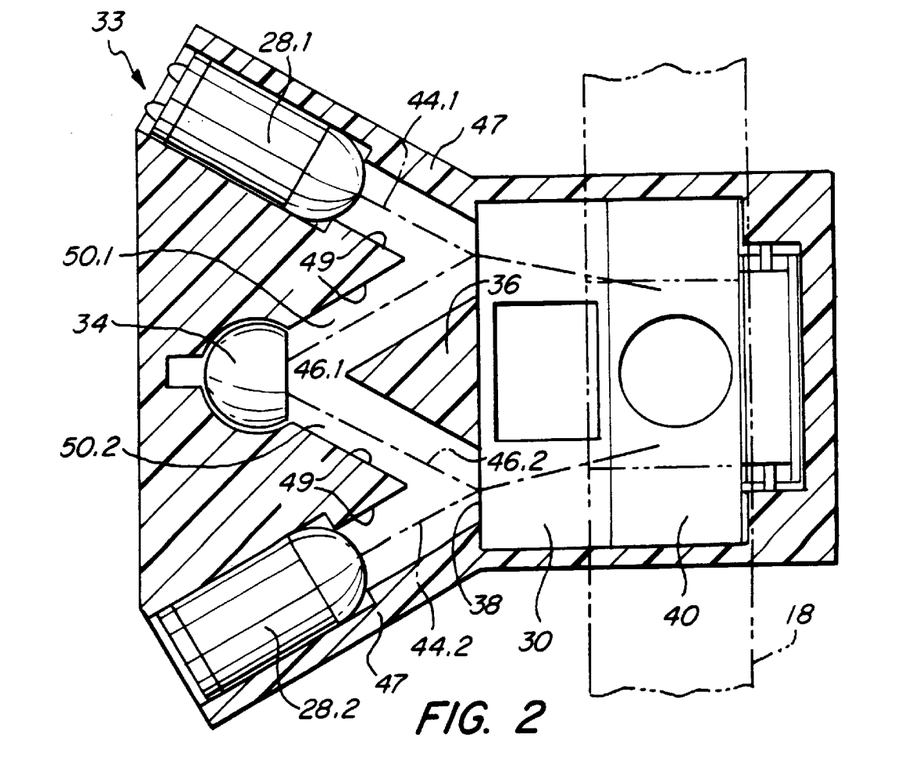
FIG. 2 is a plan view of the diagnostic instrument taken along the line 2—2 in FIG. 2.
Figure 3:
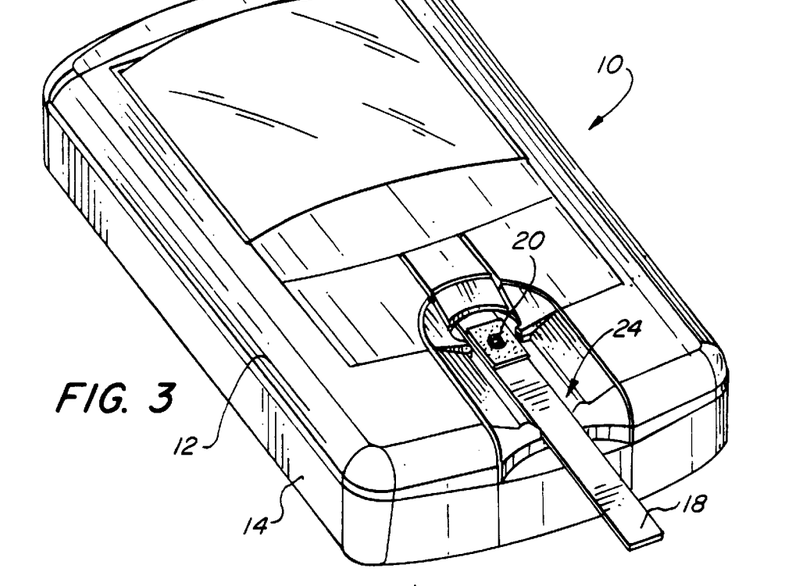
FIG. 3 is a perspective view of a diagnostic instrument in accordance with the invention.
Figure 4:
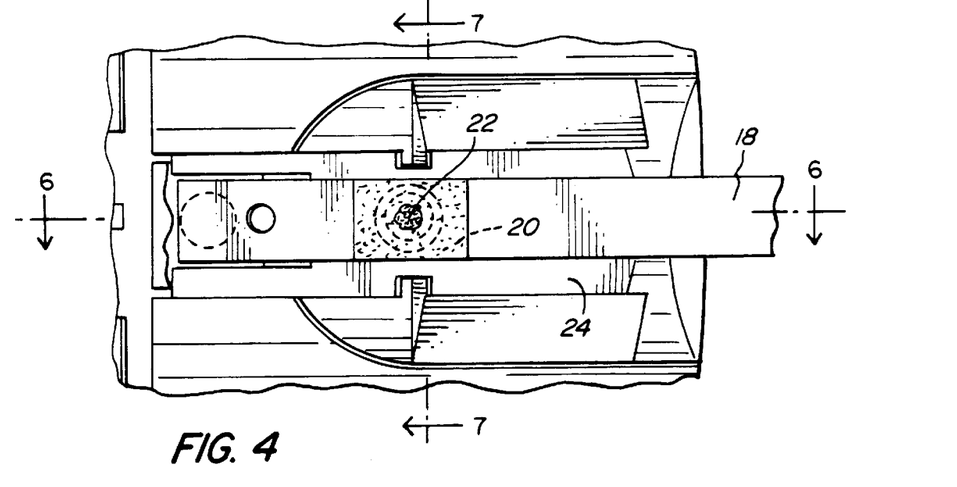
FIG. 4 is an enlarged plan view of the portion of the diagnostic instrument of FIG. 3 where a reagent strip is inserted.
Figure 5:
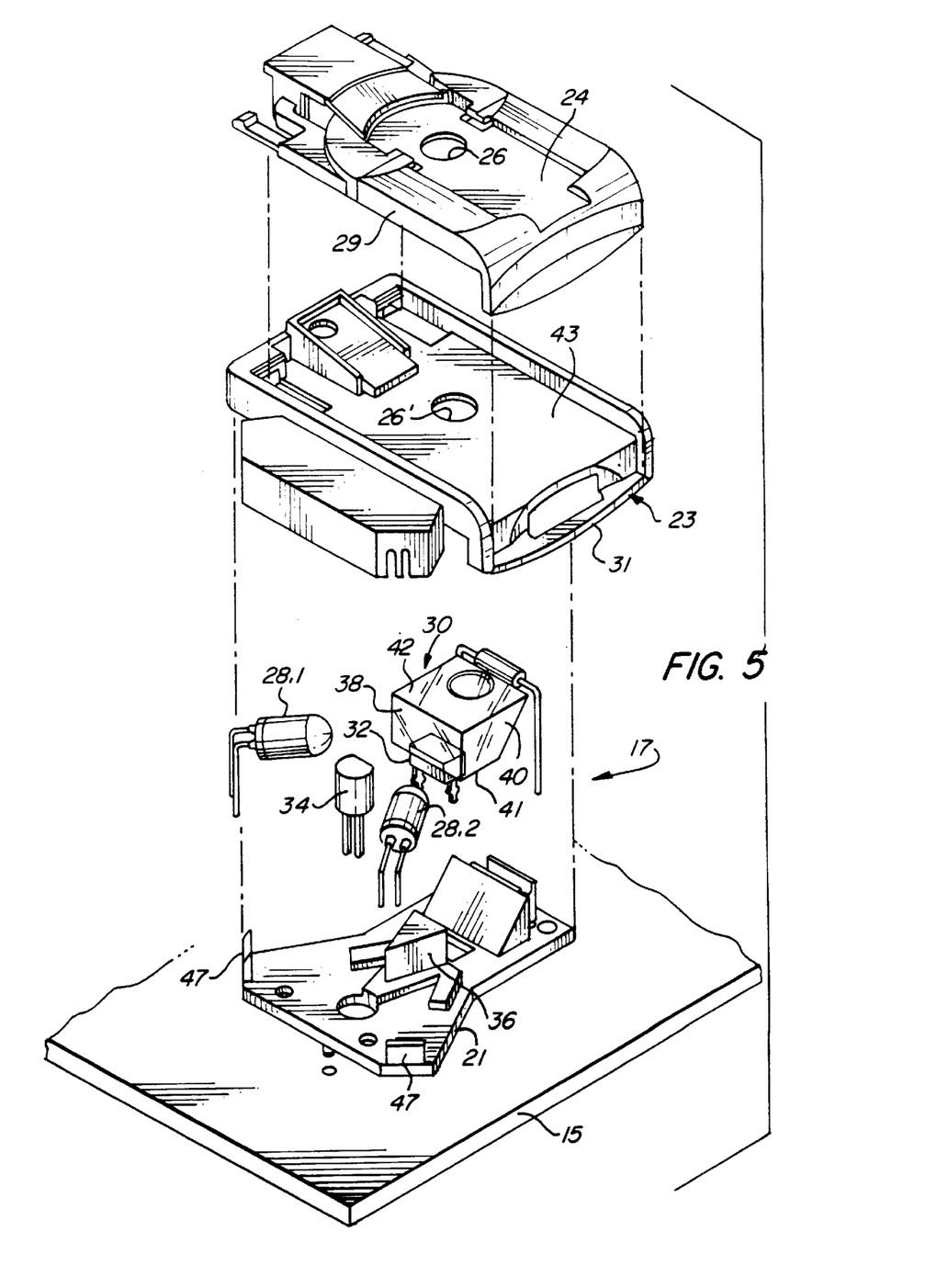
FIG. 5 is an exploded and perspective view of portions of the diagnostic instrument of FIG. 3.
Figure 6:
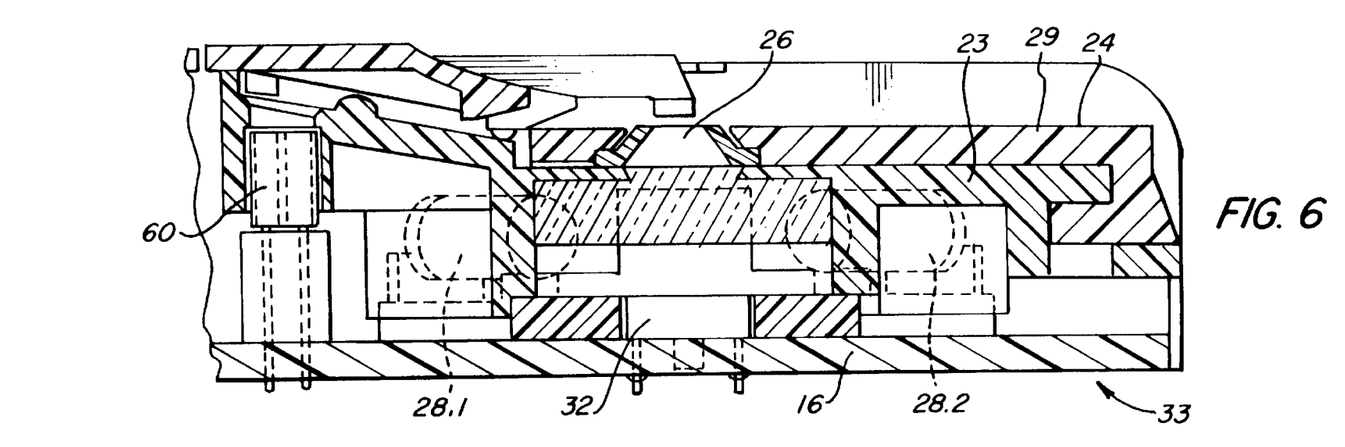
FIG. 6 is a section view of the diagnostic instrument of FIG. 3 taken along the line 6—6 in FIG. 4.
Figure 7:
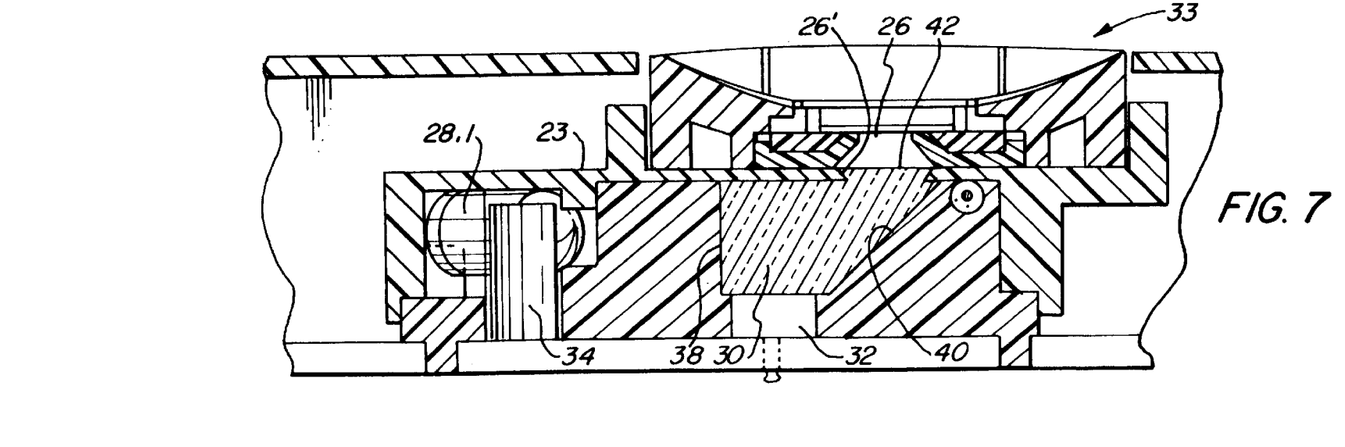
FIG. 7 is a section view of the diagnostic instrument of FIG. 3 taken along the line 7—7 in FIG. 4.
Figures 8, 9:
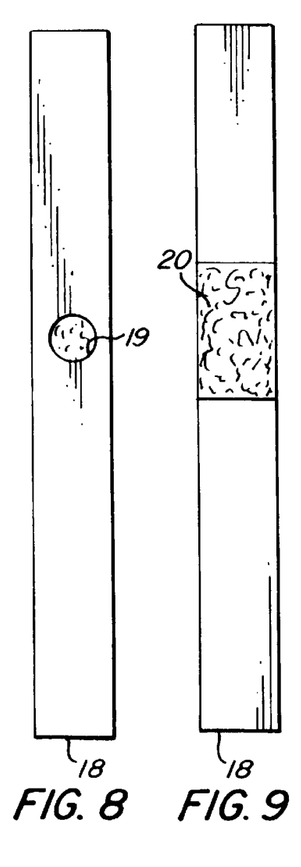
FIGS. 8, 9 and 10 are respectively back, top, and side views of a test strip for use in the instrument of FIG. 3.
Figure 10:
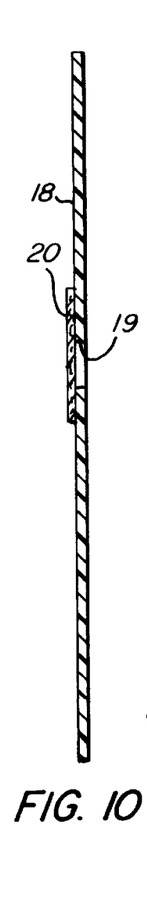
Figures 11, 12:
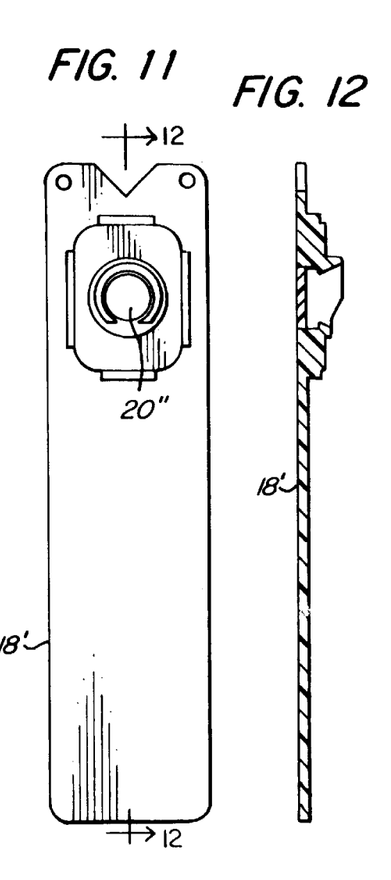
FIGS. 11, and 12 are respectively top and side views of another type of test strip for use with the instrument of FIG. 3.
Figure 13:
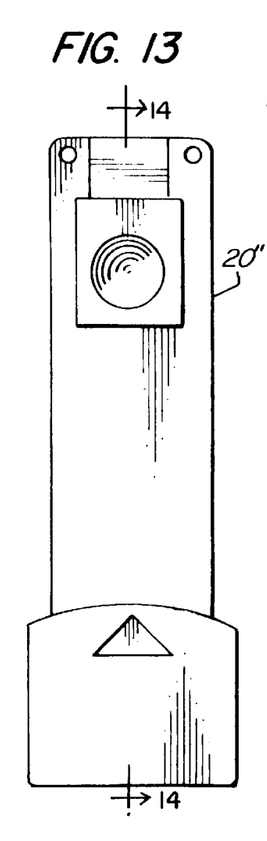
FIGS. 13 and 14 are respectively top and side views of a calibration strip for use with the instrument of FIG. 3.
Figure 14:
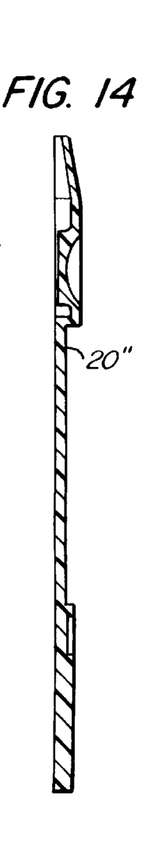

FIGS. 8, 9 and 10 show a reagent strip 18 with a reagent pad 20, bearing a reagent selected to enable the detection of glucose, and which is applied to the reagent strip 18 to overly a hole 19 through which the optical beam 25 can travel to become incident onto the reagent pad 20 reacted by a blood sample 22. FIGS. 11 and 12 show an alternative type of test strip 18' with a reagent pad 20' selected to enable the detection of fructosamine. FIGS. 13 and 14 show a standard reflectance strip 20" that can be used to calibrate the diagnostic apparatus 10 and determine whether it is operating accurately. The standard reflectance strip is placed upon the surface 24 and a diagnosis of the standard reflectance strip is made. For operation, the standard reflectance strip can have a known reflectance value at some reference wavelength.

Note that a photo-interrupter or photo- reflective sensor 60 (see FIG. 6) is used to distinguish as to what type of strip is inserted by a user into the instrument 10. The interrupter is a standard device such as sold by the Sharp company as its model GP2S22 subminiature photo-interrupter and is placed to detect the presence or insertion of a reagent strip 18 or 18'. The nature of the reflectance from the reagent material can be relied upon to determine which type of strip has been inserted.

To use the diagnostic apparatus 10, a user first turns the apparatus 10 on and then the reagent strip 18 is placed upon the surface 24. A drop of blood 22 is placed upon the reagent pad 20 of the reagent strip 18. The diagnostic apparatus 10 then makes a diagnosis of the blood sample for the presence of predetermined chemicals, such as glucose or fructosamine. The diagnostic apparatus 10 will then alert the user of the amount of those chemicals found in the blood sample.

A key aspect of the invention involves the ability to distinguish between glucose and fructosamine chemicals on blood reacted reagent pads 20. This requires a precise control over the light sources used to illuminate the reagent pads 20 even when the light sources' output wavelengths tend to shift with age, temperature and variations in current drives. Hence, a precise control over the emitted light outputs is obtained with the use of the reference photo detector 34 and a control circuit 80 as illustrated in FIG. 15 and using a photo detector having sensitivity characteristics as for example illustrated with curve 78 in FIG. 16.

Figures 15, 16:
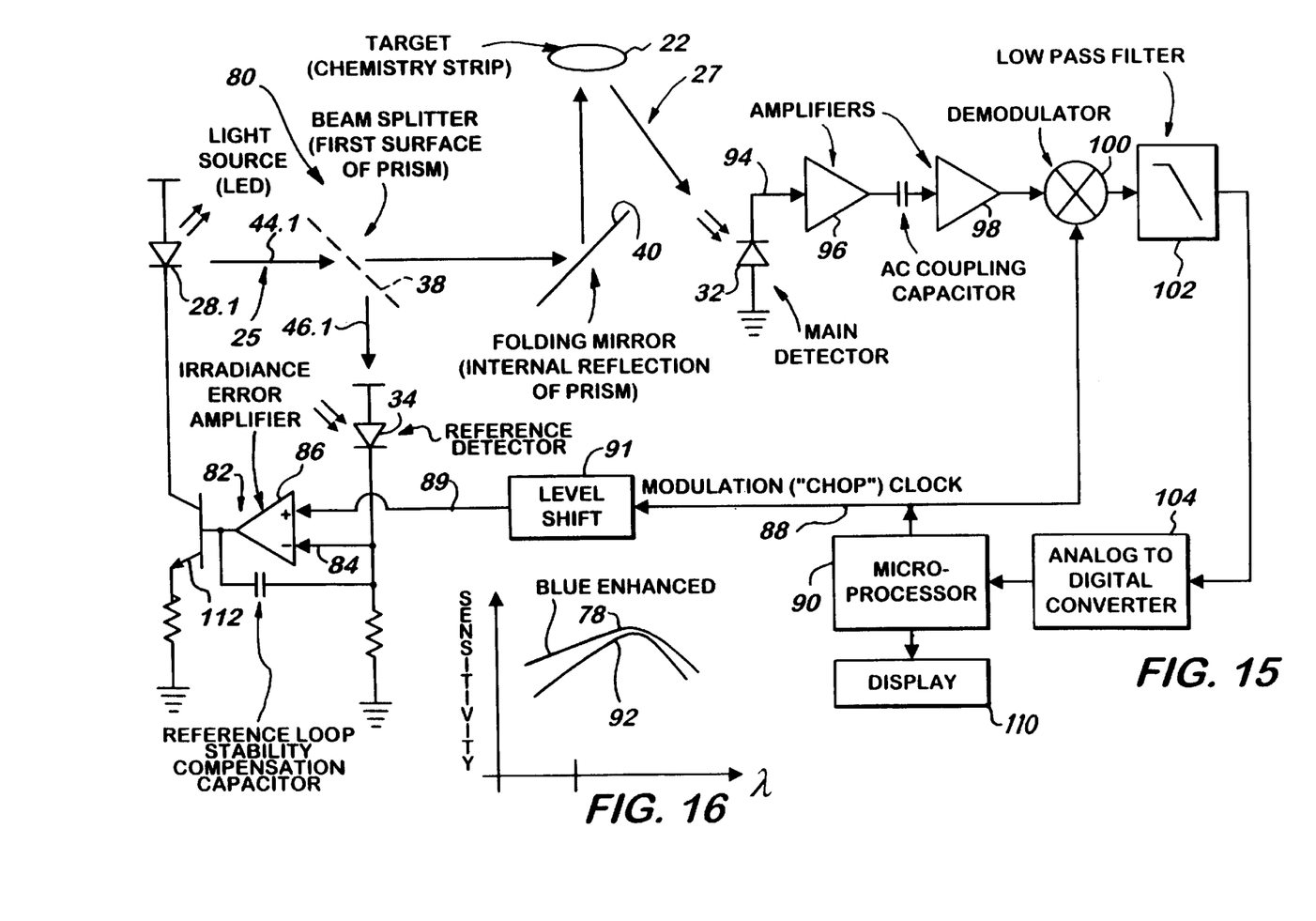
FIG. 15 is a block diagram view of a control for a light source used in the diagnostic instrument of FIG. 3.
FIG. 16 is a plot of curves of photo detectors' sensitivity as a function of wavelength.

In FIG. 15 the reference detector 34 is connected in a feedback control loop 82 to maintain the intensity output from the light source 28.1 at a constant level. This is obtained by coupling the output signal from reference detector 34 to the negative input 84 of a comparison amplifier 86 and comparing this signal with an alternating signal on line 89 that is produced by a level shifter 91 in response to a signal on line 88 from microprocessor 90. Level shifter 91 is used to set both the peak to peak amplitude and the DC bias level of the controlling signal on line 89. This DC bias level allows the control loop to compensate for interfering light sources, such as sunlight or room lights, which may be incident on reference detector 34.

When the wavelength of the light source 28.1 increases, as may happen from an increase in its temperature or in its drive current, the output of a typical silicon photo detector would also increase. As a result the reflectance measured with detector 32 would also increase as the wavelength increases, thus causing an erroneous measurement.

By using a photo detector 32 with a blue enhanced sensitivity as represented by curve 78 in comparison with an ordinary silicon type response curve 92, the sensitivity of the reference detector 34 increases more rapidly with the increased wavelength output from the light source 28.1. This increased output signal level appears as though the optical power from the light source 28.1 has increased. Since the control loop 82 is designed to maintain a constant optical output power from light source 28.1, the loop 82 reduces the output from light source 28.1 to correct for this apparent increase. A photo detector which has a blue enhanced output can be, for example, a silicon pin type photodiode identified as BPW 34B made by the Siemens Company of Germany.

When the same type of photo detector is used for the main detector 32, its sensitivity will also have increased with the increasing wavelength. This resulting increase in the main detector's output signal, however, exactly compensates for the decrease in optical power provided by the reference detector's control loop 82. Hence, the output signal from main detector 32 on line 94 represents an accurate indication of the reflectance from the reacted reagent 20 on a strip 18.

This degree of wavelength compensation can be altered by using different types of detectors 32 and 34 or by simulating different types of detectors by using different optical filters, not shown, in front of or integral to the detectors 32 or 34. For example, if the sensitivity as a function of wavelength of the main detector 32 rises more slowly with increasing wavelength than the sensitivity of the reference detector 34 (by using a blue enhanced detector for the main detector 32, for example) the main detector 32 will no longer completely make up for the reduction in optical power effected by the reference detector's control loop 82. This will lead to a decrease in the reflectance measured by the main detector 32 as the light source's wavelength increases. This decrease can be used to correct for the increase in reflectance of the test strip and any increase in transmittance of the optical system. If more or less correction is required dyes can also be added to the optical system by including an appropriate dye in the plastic molded optical element 30 during its molding to the enclosure 23.

In the embodiment illustrated in FIG. 15, one of the two light sources 28 is shown. It is to be understood that both light sources are alternately empowered and that control loop 82 is used to maintain the output power level constant for each light source 28. The sharing of the same circuitry is done by switching the empowering signal on line 88 from the microprocessor 90 and activating an appropriate switch, not shown, to energize the other light source 28.2 while de-activating light source 28.1.

Signals from the main detector 32 are suitably amplified by ac coupled amplifiers 96 and 98 and the resulting signal derived by a demodulator 100. A low pass filter 102 then provides the main detector's signal to an analog to digital converter 104 for entry and signal processing by microprocessor 90. The latter can provide an indication of the measured reflectance and chemical in a display 110. Current control through a light source 28 is obtained with a suitable transistor or other amplifier 112 placed in series with the LED 28.

Having thus described a preferred embodiment in accordance with invention its advantages can be appreciated. Variations thereof may occur to one skilled in the art. For example one skilled in the art could use more or less than two light beam generators 28 with the present invention. Different body fluids could be used to detect the presence of predetermined chemicals. Finally, the present invention can be used to detect chemicals other than glucose or fructosamine or both.

It should be understood that the foregoing is illustrative and not limiting and that obvious modifications may be made by those skilled in the art without departing from the spirit of the invention. Accordingly, reference should be made primarily to the accompanying claims, rather than the foregoing specification, to determine the scope of the invention.

What is claimed is:

1. A diagnostic instrument for generating a signal indicative of the level of a chemical in a body fluid sample using a reagent strip with a reagent which undergoes a color change when exposed to a fluid sample, comprising:

a housing having a surface for receiving reagent strips and having an optical aperture through which an optical beam from inside the housing can illuminate the reagent on the strip;

an optical beam generating structure positioned inside the housing and producing said optical beam through said optical aperture with light from a reagent strip being reflected back through said aperture for detection; said optical beam generating structure further including:

a first light source producing an optical beam directed toward said reagent strip, a reference photo detector located to detect a portion of the optical beam;

a main photo detector located to detect reflections caused by the incidence of the optical beam onto said reagent strip;

a control circuit coupled to said light source and said reference detector to maintain the light output from said light source substantially constant; and wherein said reference detector and said main detectors are so selected that a sensitivity versus wavelength characteristic of said main detector is different from a sensitivity versus wavelength characteristic of said reference detector, said reference detector being selected so that its sensitivity as a function of wavelength is sufficient to super-impose on the control circuit a compensation for changes in the wavelength of the light source and attributable to changes in the light source's drive current or operating temperature.

2. The diagnostic instrument as claimed in claim 1 wherein said reference detector is selected with a sensitivity versus wavelength characteristic that increases, at a different rate, as the wavelength from the light source increases toward longer wavelengths in comparison with the sensitivity versus wavelength characteristic for said main detector.

3. The diagnostic instrument as claimed in claim 1 and further including a control loop responsive to output signals from said reference detector and coupled to drive the optical beam generating structure in a direction so as to maintain optical power from said light beam generating structure substantially constant.

4. The diagnostic instrument as claimed in claim 1 wherein said reference detector is selected so as to have a blue wavelength enhanced sensitivity.

5. The diagnostic instrument as claimed in claim 1 wherein said reference detector includes an optical filter selected to provide said blue wavelength enhanced sensitivity.

\* \* \* \* \*